United States Patent [19]
Feingold

[11] Patent Number: 6,106,553
[45] Date of Patent: *Aug. 22, 2000

[54] INTRAOCULAR REFRACTIVE CORRECTION LENS

[75] Inventor: Vladimir Feingold, Laguna Niguel, Calif.

[73] Assignee: Staar Surgical Company, Inc., Monrovia, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/736,433

[22] Filed: Oct. 24, 1996

Related U.S. Application Data

[63] Continuation-in-part of application No. 08/318,991, Oct. 6, 1994, abandoned.

[51] Int. Cl.$^7$ .................................................. A61F 2/16
[52] U.S. Cl. ........................................................... 623/6
[58] Field of Search ...................................... 623/6

[56] References Cited

U.S. PATENT DOCUMENTS

| | | | |
|---|---|---|---|
| 4,573,998 | 3/1986 | Mazzocco | 623/6 |
| 5,104,957 | 4/1992 | Kelman et al. | 527/201 |
| 5,133,747 | 7/1992 | Feaster | 623/6 |
| 5,258,025 | 11/1993 | Fedorov et al. | 623/6 |
| 5,480,428 | 1/1996 | Fedorov et al. | 623/6 |
| 5,776,192 | 7/1998 | McDonald | 623/6 |

*Primary Examiner*—David H. Willse
*Attorney, Agent, or Firm*—Klima & Pezzlo, P.C.

[57] ABSTRACT

An artificial intraocular refractive correction lens is implanted into an eye that has a natural crystalline lens by steps of providing an artificial intraocular refractive correction lens and inserting the artificial intraocular refractive correction lens into a posterior chamber of the eye to a position anterior to and in a vicinity of the natural crystalline lens to provide a spacing between the artificial intraocular refractive correction lens and the natural crystalline lens. The implanted intraocular refractive correction lens has a shape that is predetermined with respect to a shape of the natural crystalline lens so as to form the spacing.

45 Claims, 11 Drawing Sheets

| IC2020 (POSITIVE) | | | |
|---|---|---|---|
| DIOPTER NOMINAL | Tc ± 0.05 | Do ± 0.1 | Rfr NOMINAL |
| 3.0 | 0.18 | 4.50 | 7.91 |
| 3.5 | 0.20 | 4.50 | 7.65 |
| 4.0 | 0.22 | 4.50 | 7.40 |
| 4.5 | 0.23 | 4.50 | 7.16 |
| 5.0 | 0.24 | 4.50 | 6.95 |
| 5.5 | 0.25 | 4.50 | 6.74 |
| 6.0 | 0.27 | 4.50 | 6.55 |
| 6.5 | 0.28 | 4.50 | 6.36 |
| 7.0 | 0.29 | 4.50 | 6.19 |
| 7.5 | 0.30 | 4.50 | 6.02 |
| 8.0 | 0.32 | 4.50 | 5.87 |
| 8.5 | 0.33 | 4.50 | 5.72 |
| 9.0 | 0.34 | 4.50 | 5.58 |
| 9.5 | 0.35 | 4.50 | 5.45 |
| 10.0 | 0.36 | 4.50 | 5.32 |
| 10.5 | 0.38 | 4.50 | 5.20 |
| 11.0 | 0.39 | 4.50 | 5.08 |
| 11.5 | 0.40 | 4.50 | 4.97 |
| 12.0 | 0.40 | 4.37 | 4.86 |
| 12.5 | 0.40 | 4.29 | 4.76 |
| 13.0 | 0.40 | 4.20 | 4.66 |
| 13.5 | 0.40 | 4.13 | 4.57 |
| 14.0 | 0.40 | 4.05 | 4.48 |
| 14.5 | 0.40 | 4.00 | 4.39 |
| 15.0 | 0.45 | 4.00 | 4.31 |
| 15.5 | 0.45 | 4.00 | 4.23 |
| 16.0 | 0.45 | 4.00 | 4.15 |
| 16.5 | 0.45 | 4.00 | 4.08 |
| 17.0 | 0.45 | 3.96 | 4.01 |

| IC2020 (NEGATIVE) | | | | | | |
|---|---|---|---|---|---|---|
| DIOPTER NOMINAL | Tc±0.05 | Tm±0.05 | Do±0.1 | Rfr | Rfr2 | Ro |
| | | | | NOMINAL | | |
| −3.0 | 0.21 | 0.30 | 5.0 | 13.64 | 8.93 | 10.00 |
| −3.5 | 0.20 | 0.30 | 5.0 | 14.51 | 8.93 | 10.00 |
| −4.0 | 0.19 | 0.30 | 5.0 | 15.50 | 8.93 | 10.00 |
| −4.5 | 0.17 | 0.30 | 5.0 | 16.64 | 8.93 | 10.00 |
| −5.0 | 0.16 | 0.30 | 5.0 | 17.96 | 8.93 | 10.00 |
| −5.5 | 0.14 | 0.30 | 5.0 | 19.51 | 8.93 | 10.00 |
| −6.0 | 0.13 | 0.30 | 5.0 | 21.34 | 8.93 | 10.00 |
| −6.5 | 0.12 | 0.30 | 5.0 | 23.56 | 8.93 | 10.00 |
| −7.0 | 0.10 | 0.30 | 5.0 | 26.30 | 8.93 | 10.00 |
| −7.5 | 0.09 | 0.30 | 5.0 | 29.76 | 8.93 | 10.00 |
| −8.0 | 0.07 | 0.30 | 5.0 | 34.26 | 8.93 | 10.00 |
| −8.5 | 0.06 | 0.30 | 5.0 | 40.38 | 8.93 | 10.00 |
| −9.0 | 0.12 | 0.35 | 4.8 | 49.18 | 8.76 | 10.00 |
| −9.5 | 0.10 | 0.35 | 4.8 | 62.83 | 8.76 | 10.00 |
| −10.0 | 0.09 | 0.35 | 4.8 | 86.99 | 8.76 | 10.00 |
| −10.5 | 0.08 | 0.35 | 4.8 | 141.34 | 8.76 | 10.00 |
| −11.0 | 0.07 | 0.35 | 4.8 | 376.86 | 8.76 | 10.00 |
| −11.5 | 0.09 | 0.35 | 4.5 | 100000 | 8.78 | 9.83 |
| −12.0 | 0.08 | 0.35 | 4.5 | 100000 | 8.78 | 9.42 |
| −12.5 | 0.07 | 0.35 | 4.5 | 100000 | 8.78 | 9.04 |
| −13.0 | 0.10 | 0.40 | 4.5 | 100000 | 8.61 | 8.69 |
| −13.5 | 0.09 | 0.40 | 4.5 | 100000 | 8.61 | 8.37 |
| −14.0 | 0.08 | 0.40 | 4.5 | 100000 | 8.61 | 8.07 |
| −14.5 | 0.07 | 0.40 | 4.5 | 100000 | 8.61 | 7.79 |
| −15.0 | 0.11 | 0.45 | 4.5 | 100000 | 8.46 | 7.53 |
| −15.5 | 0.09 | 0.45 | 4.5 | 100000 | 8.46 | 7.29 |
| −16.0 | 0.08 | 0.45 | 4.5 | 100000 | 8.46 | 7.06 |
| −16.5 | 0.07 | 0.45 | 4.5 | 100000 | 8.46 | 6.85 |
| −17.0 | 0.06 | 0.45 | 4.5 | 100000 | 8.46 | 6.65 |

|  |  |  |  |
|---|---|---|---|
|  |  | Example – (100ph2, – 10 Diopter) |  |
|  |  |  |  |
|  |  | R1[mm] | 100000.00 |
|  |  | R2[mm] | 11.96 |
|  |  | R3[mm] | 13.60 |
|  |  | R4[mm] | 15.75 |
|  |  | R5[mm] | 18.70 |
|  |  | R6[mm] | 10.00 |
|  |  | R7[mm] | 8.96 |

INTRAOCULAR REFRACTIVE CORRECTION LENS

RELATED APPLICATIONS

This application is a continuation-in-part U.S. patent application entitled "Intraocular Contact Lens", Ser. No. 08/318,991, filed Oct. 6, 1994, now abandoned, and incorporated herein by reference.

FIELD OF THE INVENTION

This invention relates to an intraocular lens, in particular an intraocular refractive correction lens, and a method of implanting an intraocular lens to correct the eyesight of an eye.

BACKGROUND OF THE INVENTION

Major ocular components of an eye include a retina and cornea. The cornea connects to the sclera at the limbus. An anterior segment of the eye is divided into two principle chambers by the iris and pupil. An anterior chamber is defined by the space between the cornea and the iris. A posterior chamber is defined by the space between the iris and vitreous.

A natural crystalline lens is located behind the pupil as defined by the iris. The natural crystalline lens is attached at its periphery by zonules. The eye is deformable and the zonule attachments allow the natural crystalline lens to deform to different optical powers. In some cases, the natural crystalline lens does not properly deform to achieve a required focus or the length of the eyeball is such that an image does not fall directly on the retina. Spectacles or contact lenses are required to compensate for the focus of the natural lens or axial length of the eye. Recent technological developments have provided a deformable and relatively permanent artificial intraocular lens that can be implanted into the eye to provide permanent vision correction. An intraocular lens has an optical zone portion and is generally made of flexible material suitable for optical use such as silicone.

At least two general problems are associated with implantation of an intraocular lens. First, the implantation method requires a relatively large incision, which can lead to complications such as infection, retinal detachment and laceration of the ocular tissue. A second problem relates to the intraocular environment. Intraocular tissue is extremely delicate and sensitive. Any artificial body that is inserted into the eye must be designed with consideration of the body's interface with intraocular tissue on all surfaces, not just one surface as with an exterior, surface contact lens. Further, intraocular tissue differs from exterior eye tissue. At least one surface of exterior eye tissue is exposed to the hardening influence of an exterior environment, which at least to some extent enures the one surface to the effect of foreign bodies such as a surface contact lenses.

U.S. Pat. Nos. 4,573,998 and 4,702,244 both to Mazzocco, disclose an improved intraocular lens structure, method and instrumentation for implantation through a relatively small incision in ocular tissue. The disclosures of the U.S. Pats. No. 4,573,998 and 4,702,244 are incorporated herein by reference. The lens structure disclosed in the U.S. Pat. Nos. 4,573,990 and 4,702,244 comprises a deformable optical zone portion having prescribed memory characteristics. The lens can be deformed by compressing, rolling, folding, stretching or by a combination thereof to a small diameter for insertion through a small incision in the eye. The memory characteristics enable the lens to return to an original configuration with full size and fixed focal length after insertion. The optical zone portion of the lens is fabricated from a biologically inert material possessing elasticity and compression characteristics.

Copending parent application, Ser. No. 08/318,991 to Feingold addresses a problem of shape of an intraocular lens with regard to the intraocular environment. The disclosure of this application is incorporated herein by reference.

Feingold teaches an intraocular contact lens provided with an outer radius of curvature between a lens body portion (base portion) and a lens portion (optic portion) that smoothly transitions therebetween. Specifically, there exists a transition in the outer radius of curvature of the lens between the lens base portion and the optic portion. It is important that the transition in the radius of curvature between these two portions or zones is such that there is a minimization of edge formation so as to prevent damage or wear to the back of the iris. A transition can be made that has a gradient of radius of curvature within very small dimensions. The transition forms a transition portion that defines an elliptically transcribed surface transition from the surface of the optic portion to the surface of the base portion. Such an arrangement works well within the eye and does not appear to damage or wear the back of the iris.

Feingold also teaches that at least one groove can be provided in the outer surface of the intraocular contact lens. The groove is preferably in the arrangement of a circular groove located in the base portion and surrounding the optic portion. The circular groove allows for good circulation of eye fluid to facilitate lubrication between the intraocular contact lens and the back of the iris. Other groove configurations can be utilized.

Further, Feingold teaches that a passageway can be provided in the intraocular lens between posterior and anterior surfaces to equalize intraocular pressure against the lens surfaces to allow equalization of pressure between anterior and posterior eye chambers. The passageway is provided in a variety of different forms. The passageway can be in the form of a groove in the anterior surface and a groove in the posterior surface that connect to form a continuous channel or the passageway can be provided in the form of a hole through the thickness dimension of the intraocular lens at one or more locations.

Feingold also provides one or more through holes in the iris to place the anterior chamber and posterior chamber in fluid communication to allow equalization of pressure therebetween. This prevents the intraocular contact lens from being sucked into tight contact with the back of the iris to cause damage and wear to the back of the iris. The tight contact effect is due to a differential pressure between the posterior and anterior eye chambers. The through holes eliminate the differential pressure between the chambers.

Figure 25:
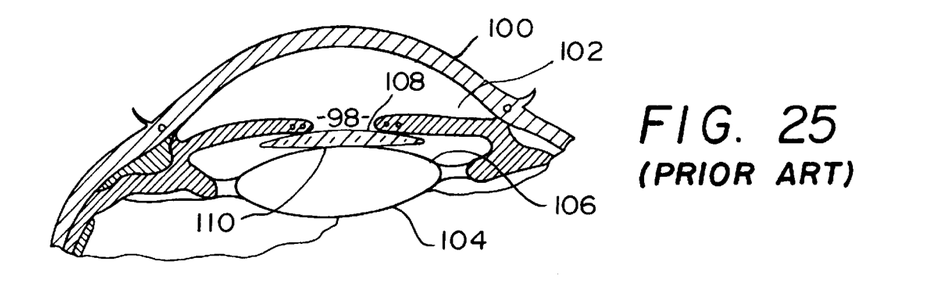
FIG. 25 is a partial side sectional view of a human eye with an artificial intraocular lens illustrating a lens implant of the prior art.

FIG. 25 is a partial side sectional view of a human eye showing a location of an implanted intraocular contact lens. The lens is located in the posterior chamber and can be fixed in the chamber by a peripheral body member (haptic), which extends beyond the optic portion of the lens. The body member accomplishes fixation by contacting the peripheral tissues of the eye posterior to the iris in the area of the ciliary sulcus. The posterior surface of the lens intimately contacts the convex anterior surface of the lens.

One problem with this arrangement is that the intimate contact between surfaces of the implanted lens and the natural crystalline lens can cause cataracts. It is desirable to place the intraocular lens in a position with respect to the natural lens that minimizes contact between surfaces of the implanted lens and the natural crystalline lens to reduce the risk of cataracts. Heretofore however, it has been believed necessary to intimately contact the two surfaces in order to achieve proper refractive correction. The present invention is based in part on a finding that proper refractive correction can be achieved and at the same time, development of cataracts can be avoided by implanting an intraocular lens so as to form a spacing between the posterior surface of the intraocular lens and the anterior surface of the natural crystalline lens.

SUMMARY OF THE INVENTION

An object of the invention is to provide an improved intraocular lens in the form of an intraocular refractive correction lens and improved method of implanting the intraocular refractive correction intraocular lens.

A further object is to provide an intraocular refractive correction lens that forms a spacing with the natural crystalline lens of the eye when the intraocular refractive correction lens is implanted into the eye.

A further object is to provide an intraocular refractive correction lens that cooperates with the natural crystalline lens to correct eyesight.

A further object of the present invention is to provide an intraocular refractive correction lens that remains comfortably fitted into the eye over extended periods of time.

A further object of the present invention is to provide an improved method of implantation of an intraocular refractive correction lens.

These and other objects of the present invention are described in detail in the description of the invention taken in conjunction with the drawings.

The invention relates to a method of implanting an artificial intraocular refractive correction lens into an eye having a natural crystalline lens and pupil. The method comprises steps of providing an artificial intraocular refractive correction lens and inserting the artificial intraocular refractive correction lens into a posterior chamber of the eye to a position anterior to and in a vicinity of the natural crystalline lens in the location of the pupil to provide a spacing between the artificial intraocular refractive correction lens and the natural crystalline lens.

The invention also relates to an intraocular refractive correction lens implanted in a posterior chamber of an eye in a vicinity of the natural crystalline lens. The intraocular refractive correction lens comprises a shape predetermined with respect to a shape of the natural crystalline lens to form a spacing between a posterior surface of the intraocular refractive correction lens and an anterior surface of the natural crystalline lens.

The invention also relates to an intraocular refractive correction lens for implanting in the vicinity of a natural crystalline lens of an eye. The intraocular refractive correction lens comprises a shape that is predetermined with respect to a shape of the natural crystalline lens to form a spacing between a posterior surface of the intraocular refractive correction lens and an anterior surface of the natural crystalline lens when the intraocular refractive correction lens is implanted into the eye.

DETAILED DESCRIPTION OF THE PREFERRED EMBODIMENTS

The intraocular lens of the invention has a concave posterior face that is shaped substantially complementary to the convex shape of the anterior surface of the natural crystalline lens. The intraocular lens is adapted to provide a face to face relationship with the anterior surface of the natural crystalline lens. However, as hereinafter described, at least a part of the posterior surface of the intraocular lens is separated from the anterior surface of the natural crystalline lens to form a spacing between the intraocular lens and the natural crystalline lens. The spacing is formed at a location between the intraocular lens and the pupil of the eye.

Figure 1:
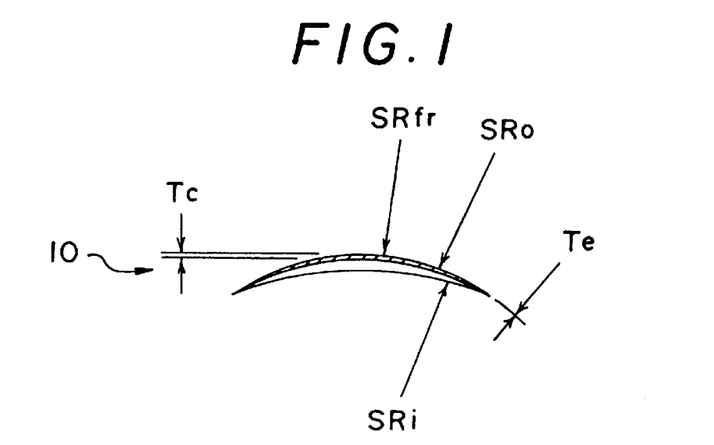
FIG. 1 is a cross-sectional view of a positive intraocular refractive correction lens, as indicated in FIG. 3.
Figure 2:
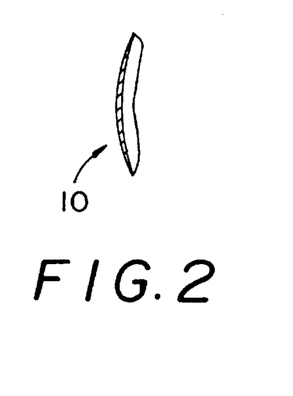
FIG. 2 is a cross-sectional view of the intraocular lens in FIG. 1, as indicated in FIG. 3.
Figure 3:
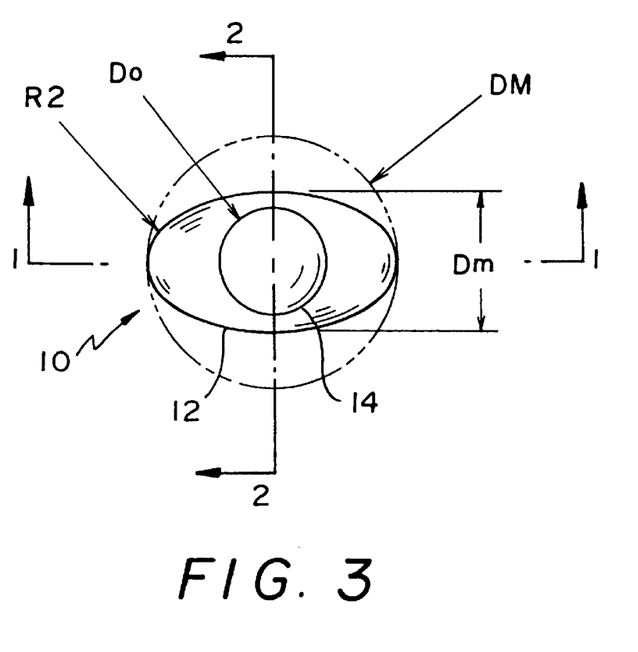
FIG. 3 is a top planar view of the positive intraocular refractive correction lens as shown in FIGS. 1 and 2.

An embodiment of a positive intraocular refractive correction lens according to the present invention is shown in FIGS. 1–3.

The intraocular refractive correction lens 10 is defined by an oval-shaped lens body portion 12 defined by major axis diameter DM and minor axis diameter Dm, and radius R2, and a circular shaped lens portion 14 having a diameter Do.

The lens portion 14 has a thickness Tc and the lens body portion 12 has an edge thickness Te, as shown in FIG. 1. Further, the lens portion 14 has a curvature SRfr, and the lens body portion 12 has an outer curvature SRo and an inner curvature SRi.

Figure 4:
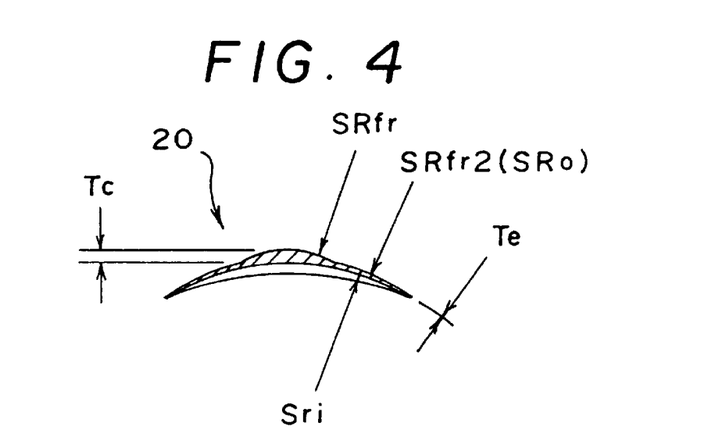
FIG. 4 is a cross-sectional view of another embodiment of a positive intraocular refractive correction lens as indicated in FIG. 6.
Figure 5:
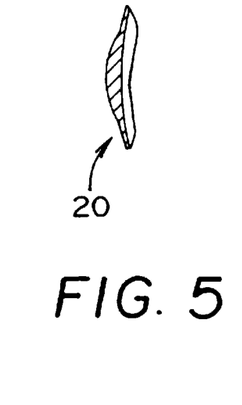
FIG. 5 is a cross-sectional view of the positive intraocular refractive correction lens shown in FIG. 4, as indicated in FIG. 6.
Figure 6:
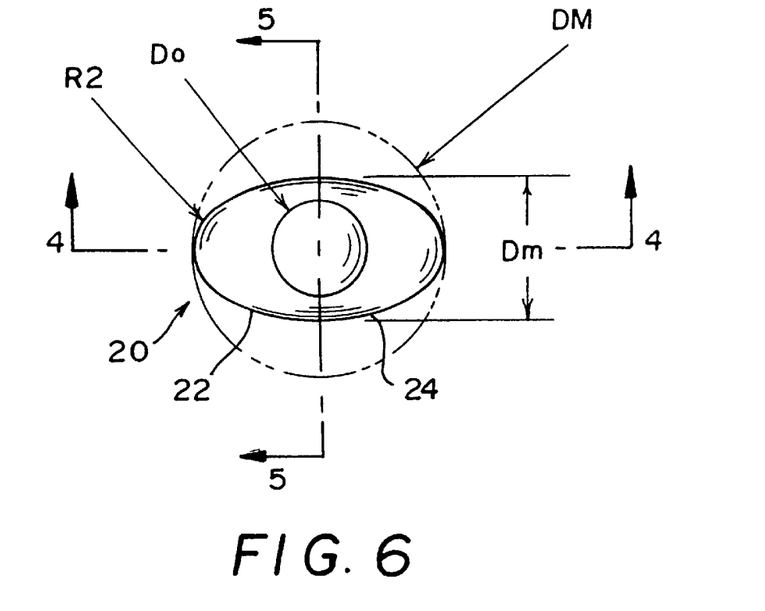
FIG. 6 is a top planar view of the positive intraocular refractive correction lens as shown in FIGS. 4 and 5.

Another embodiment of a positive intraocular refractive correction lens according to the present invention as shown in FIGS. 4–6.

The intraocular refractive correction lens 20 is defined by an oval-shaped lens body portion 22 defined by major axis diameter DM and minor axis diameter Dm, and a radius R2, and a circular shaped lens portion 24 having a diameter Do.

The lens portion 24 has a thickness Tc and the lens body portion 22 has an edge thickness Te, as shown in FIG. 4. Further, the lens portion 24 has a curvature SRfr and the lens body portion 22 has an outer curvature SRfr2 (SRo) and an inner curvature SRi.

Figure 7:
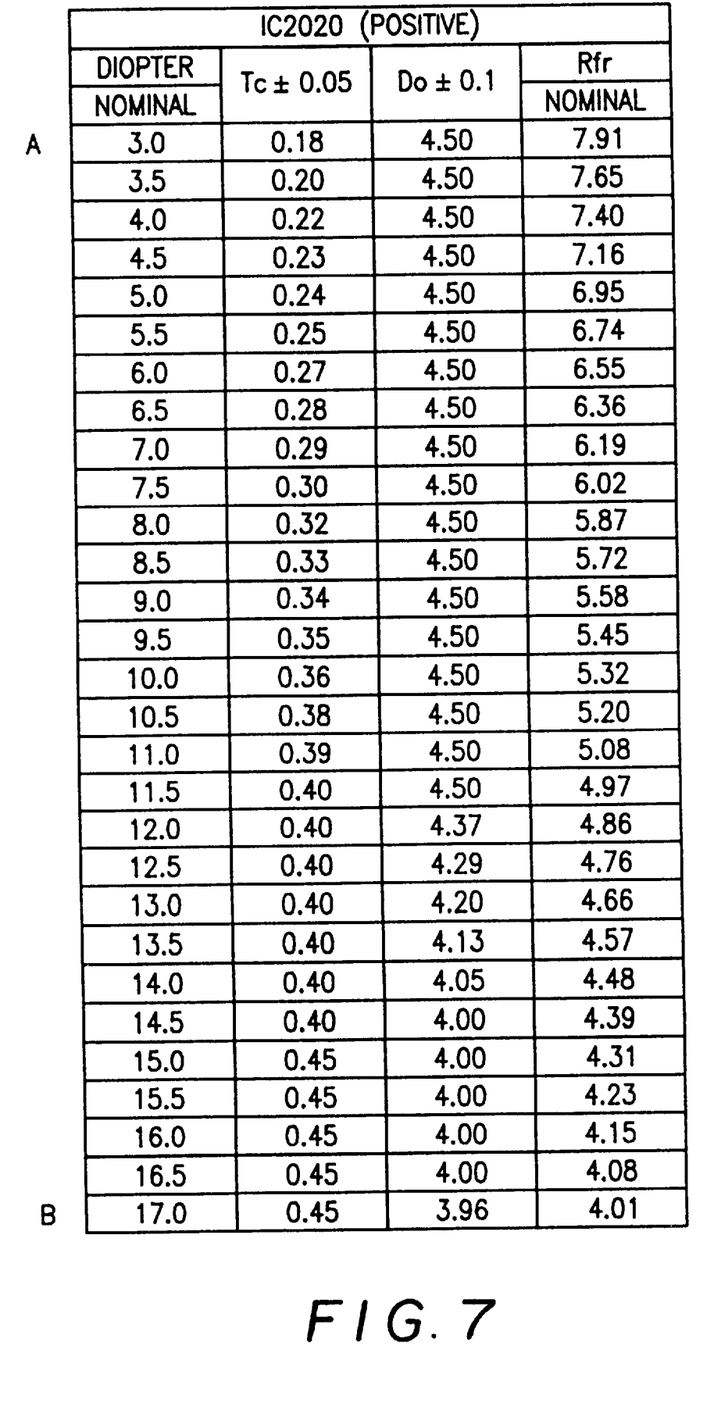
FIG. 7 is a table of examples of positive intraocular refractive correction lenses directed to the two embodiments shown in FIGS. 5–10.

Specific examples of the positive intraocular refractive correction lens are given in the table in FIG. 7. In these examples, T=0.05±0.02 mm, Sro=9.4±0.1, SRi=9.8, DM=10.5±0.1 mm, Dm=6±0.3 mm and R2+0.1.

Figure 8:
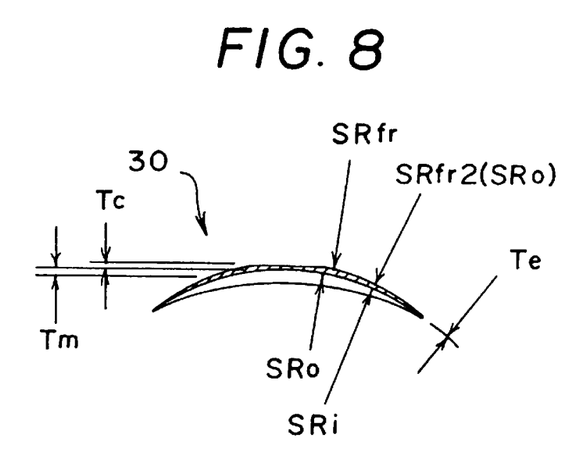
FIG. 8 is a cross-sectional view of a negative intraocular refractive correction lens according to the present invention, as indicated in FIG. 10.
Figure 9:
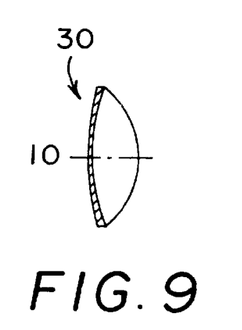
FIG. 9 is a cross-sectional view of the negative intraocular refractive correction lens shown in FIG. 8, as indicated in FIG. 10.
Figure 10:
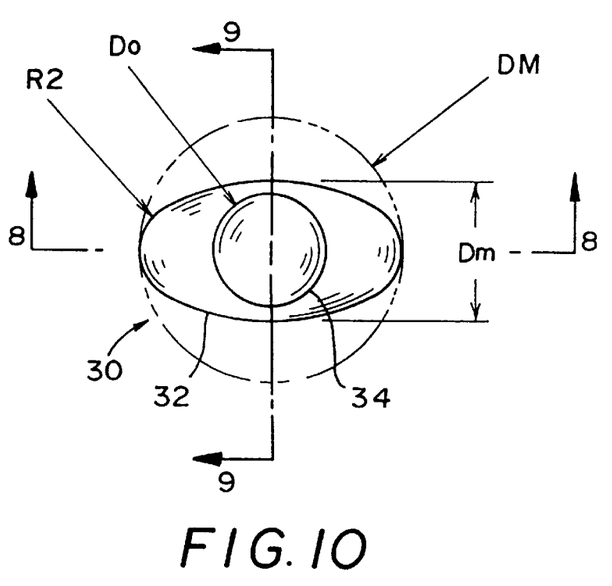
FIG. 10 is a top planar view of the negative intraocular contact lens shown in FIGS. 8 and 9.

An embodiment of a negative intraocular refractive correction lens according to the present invention as shown in FIGS. 8–10.

The intraocular refractive correction lens 30 is defined by an oval-shaped lens body portion 32 defined by major axis diameter DM and minor axis diameter Dm, and having a radius R2, and a circular shaped lens portion 34 having a diameter Do.

The lens portion 34 has a thickness Tc and the lens body portion 32 has an edge thickness Te, as shown in FIG. 8. Further, the lens portion 34 has a curvature SRfr and the lens body portion 32 has an outer curvature SRo and an inner curvature SRi.

Figure 11:
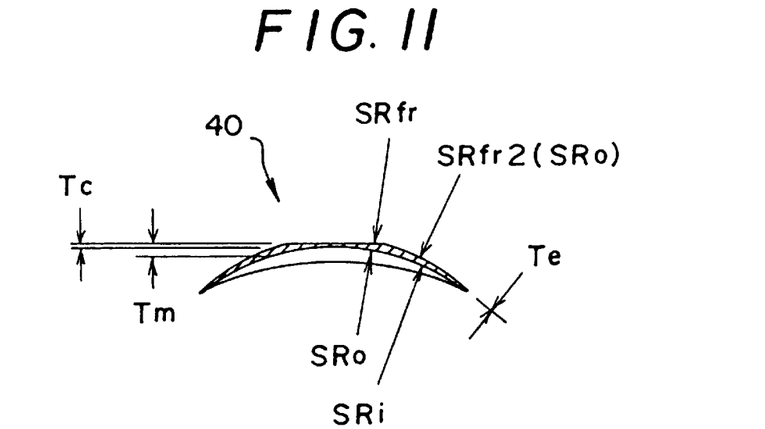
FIG. 11 is another embodiment of a negative intraocular refractive correction lens according to the present invention, as indicated in FIG. 12.
Figure 12:
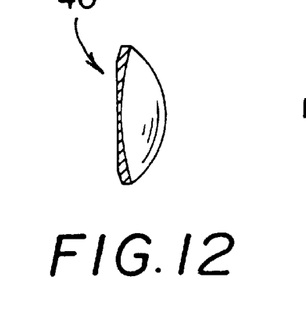
FIG. 12 is a cross-sectional view of the intraocular lens shown in FIG. 11, as indicated in FIG. 13.
Figure 13:
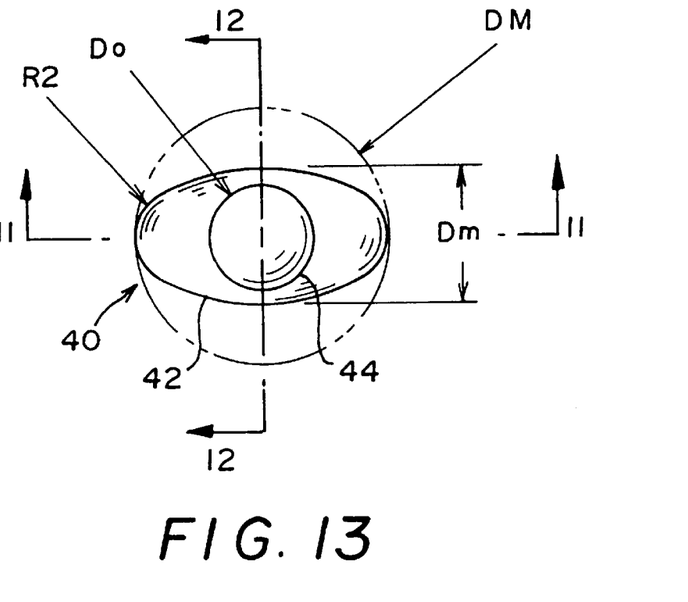
FIG. 13 is a top planar view of the negative intraocular refractive correction lens shown in FIGS. 11 and 12.

Another embodiment of a negative intraocular refractive correction lens according to the present invention as shown in FIGS. 11–13.

The intraocular refractive correction lens 40 is defined by an oval-shaped lens body portion 42 defined by major axis diameter DM and minor axis diameter Dm, and having a radius R2, and a circular shaped lens portion 44 having a diameter Do.

The lens portion 44 has a thickness Tc and the lens body portion 42 has an edge thickness Te, as shown in FIG. 11. Further, the lens portion 44 has a curvature SRfr and the lens body portion 42 has an outer curvature SRfr2 (SRo) and an inner curvature SRi.

Figure 14:
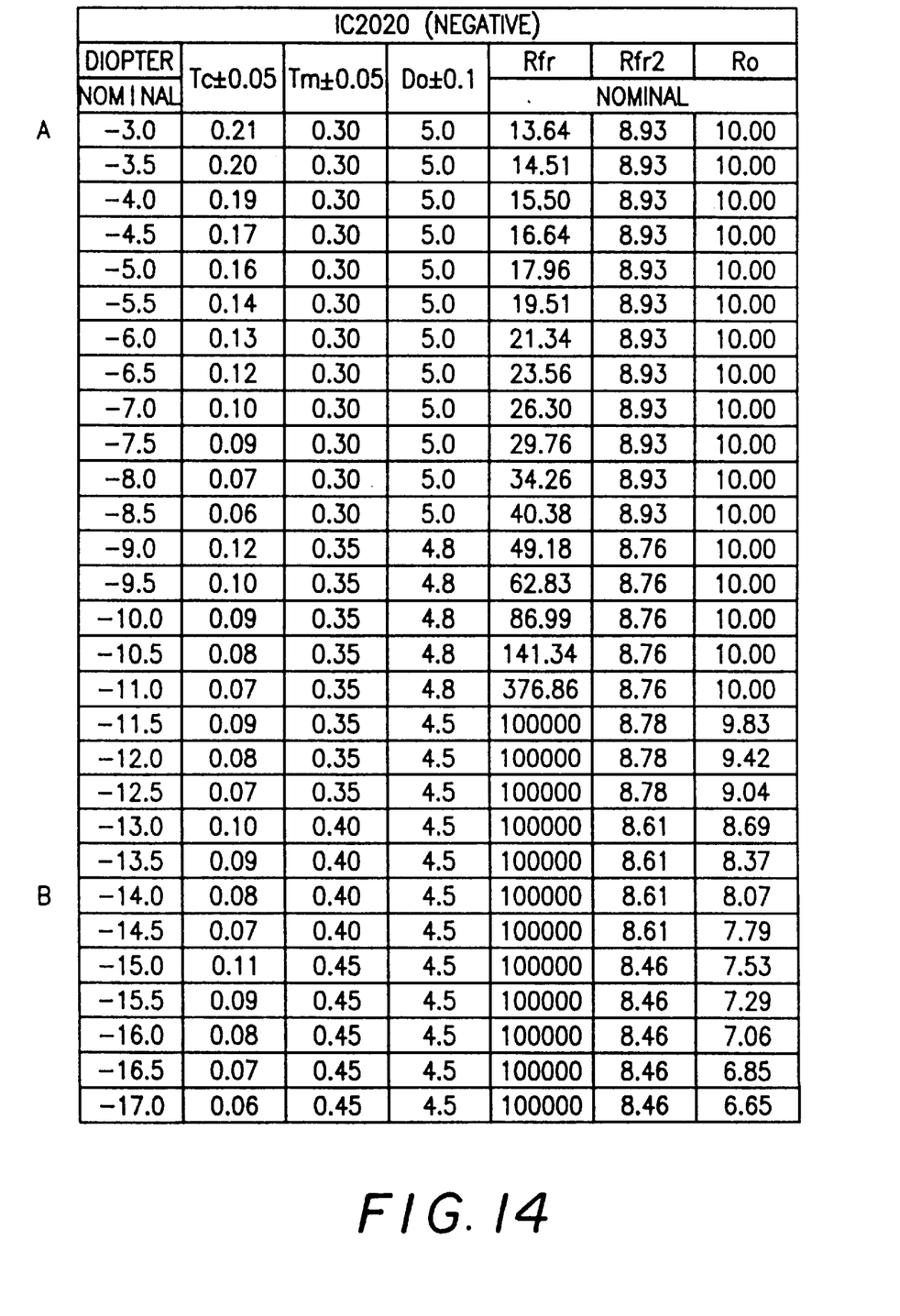
FIG. 14 is a table of examples of negative intraocular lenses directed to the two embodiments shown in FIG. 8–13.

Specific examples of the positive intraocular refractive correction lens are given in the table in FIG. 14. In these examples, T=0.05±0.02 mm, Sro=9.4±0.1, SRi=9.8, DM=10.5±0.1 mm, Dm=6±0.3 mm and R2±0.1. When the value of Rfr reaches 100,000 mm, as shown in FIG. 14, the anterior surface of the optic portion of the lens is essentially planar, as it appears in FIG. 11.

Figure 15:
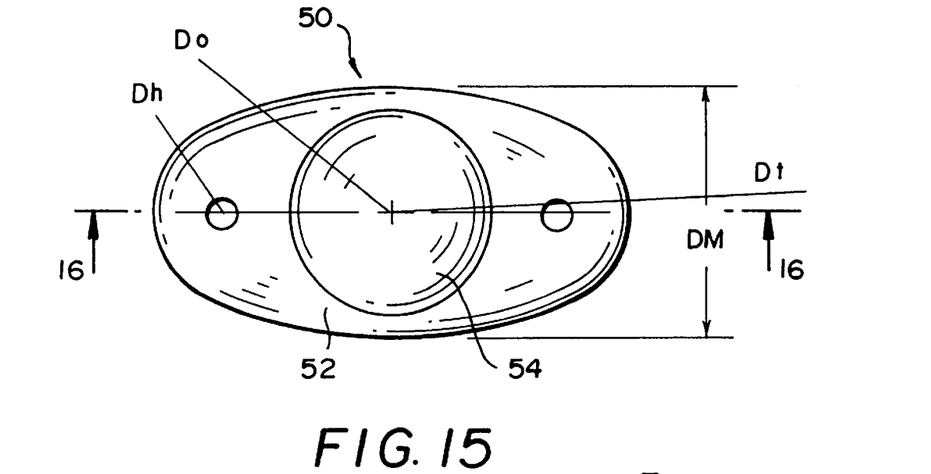
FIG. 15 is a top planar view of another embodiment of a positive intraocular refractive correction lens according to the present invention.
Figure 16:
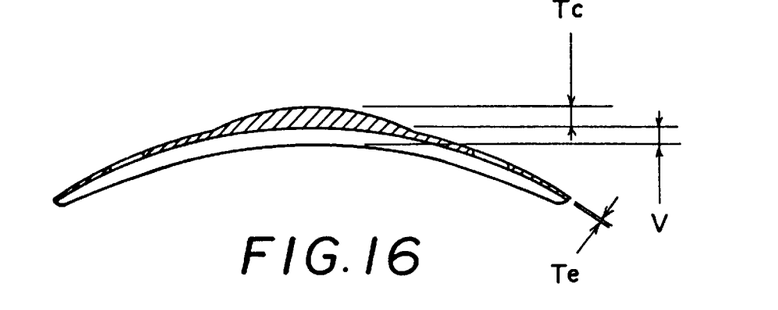
FIG. 16 is a cross-sectional view of the positive intraocular refractive correction lens, as indicated in FIG. 15.
Figure 17:
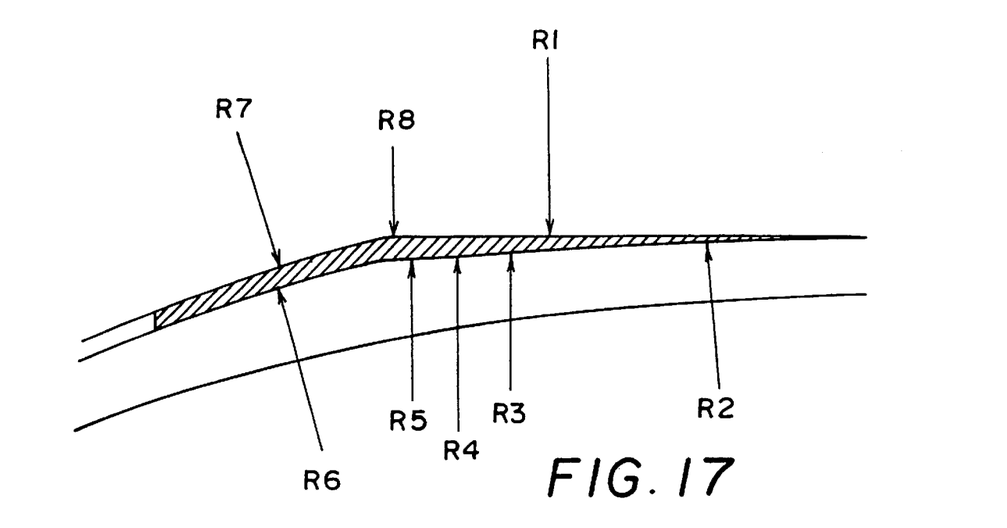
FIG. 17 is a partial detailed cross-sectional view of a portion of the positive intraocular lens shown in FIGS. 15 and 16, illustrating the detailed curvature thereof.

A further embodiment of a positive intraocular refractive correction lens 50 is shown in FIGS. 15–17.

The intraocular refractive correction lens 50 is defined by an oval-shaped lens body portion 52 defined by major axis diameter DM and minor axis diameter Dm, and radius R2, and a circular shaped lens portion 54 having a diameter Do. The lens portion 54 has a thickness Tc and the lens body portion 52 has an edge thickness Te, as shown in FIG. 16.

Figure 18:
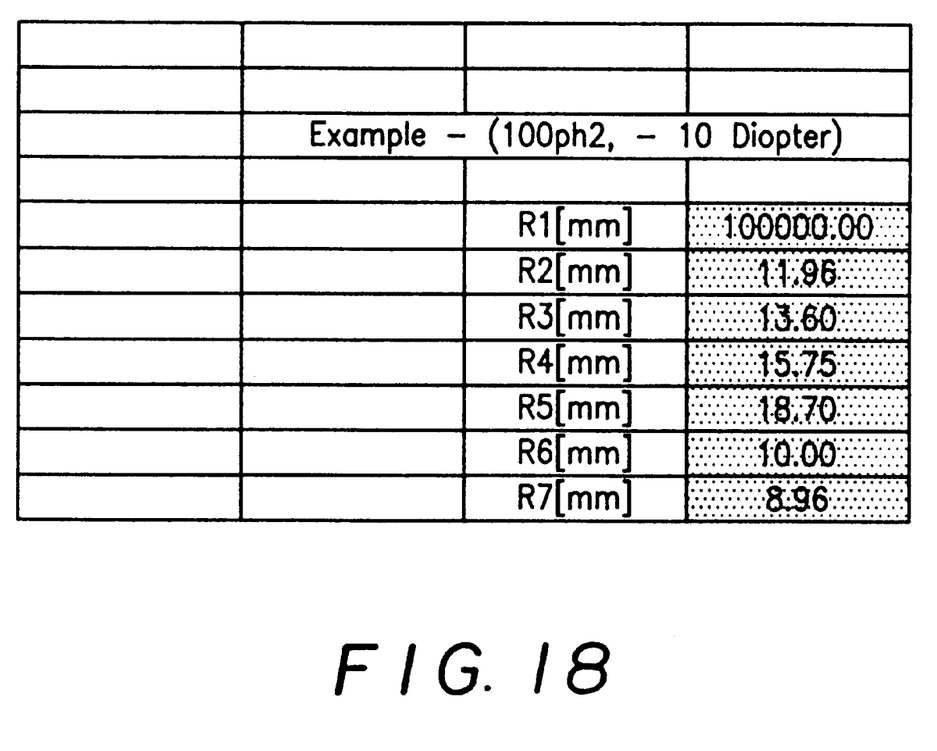
FIG. 18 is a table indicating the detailed curvature as an example of the embodiment of the positive intraocular lens shown in FIGS. 15–17.

The detailed curvature of the intraocular refractive correction lens is shown in FIG. 17. An example of this particular lens is given in the table in FIG. 18 with the designations R1–R8 corresponding to FIG. 17.

Figure 19:
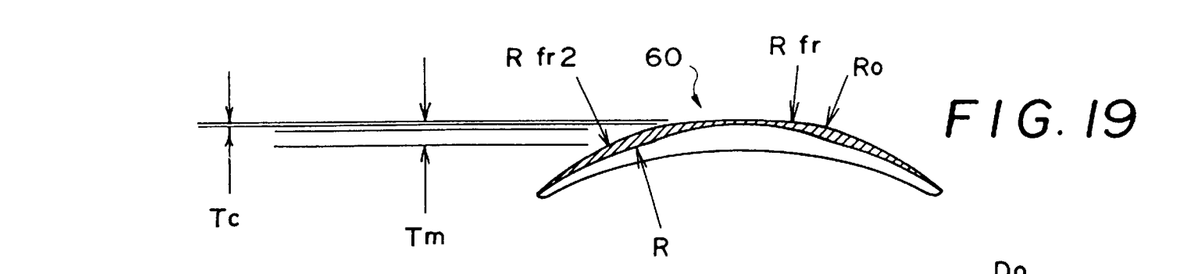
FIG. 19 is another embodiment of a negative intraocular refractive correction lens according to the present invention.

A further embodiment of a negative intraocular refractive correction lens 60 is shown in FIG. 19. The advantage of this embodiment is that a small gap exists between the intraocular refractive correction lens center and the natural lens allowing for flow of body fluids, and to minimize friction which could potentially cause mechanical damage and cataracts in the eye.

Figure 20:
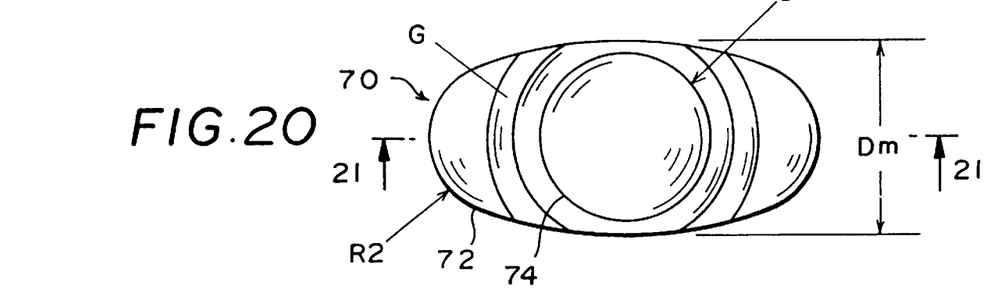
FIG. 20 is a top planar view of another negative intraocular refractive correction lens according to the present invention with a circular groove in the lens body portion thereof.

An even further embodiment of a negative intraocular refractive correction lens 70 is shown in FIG. 20.

Figure 21:
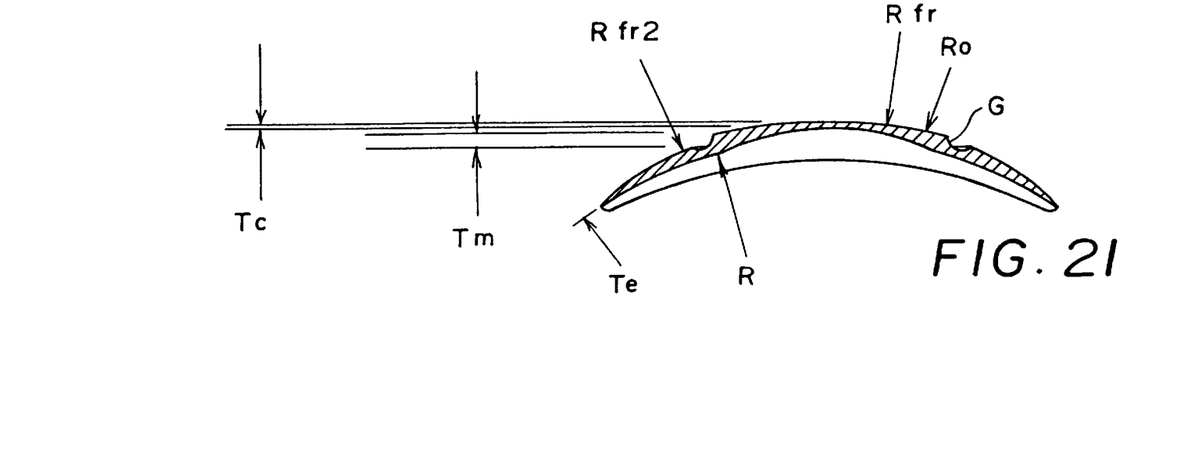
FIG. 21 is a cross-sectional view of the negative intraocular refractive correction lens, as indicated in FIG. 20.

The intraocular refractive correction lens 70 is defined by an oval-shaped lens body portion 72 defined by major axis diameter DM and minor axis diameter Dm, and a circular shaped lens portion 74 having a diameter Do. The lens portion 74 has a thickness Tc and the lens body portion 72 has an edge thickness Te, as shown in FIG. 21.

The important feature of this embodiment is the circular groove G provided in the lens body portion 72 surrounding the lens portion 74. The circular groove G allows for circulation of fluid inside the eye. Further, the groove G can be used for lens manipulation during surgery, and facilitates the equalization of intraocular pressure.

Figure 22:
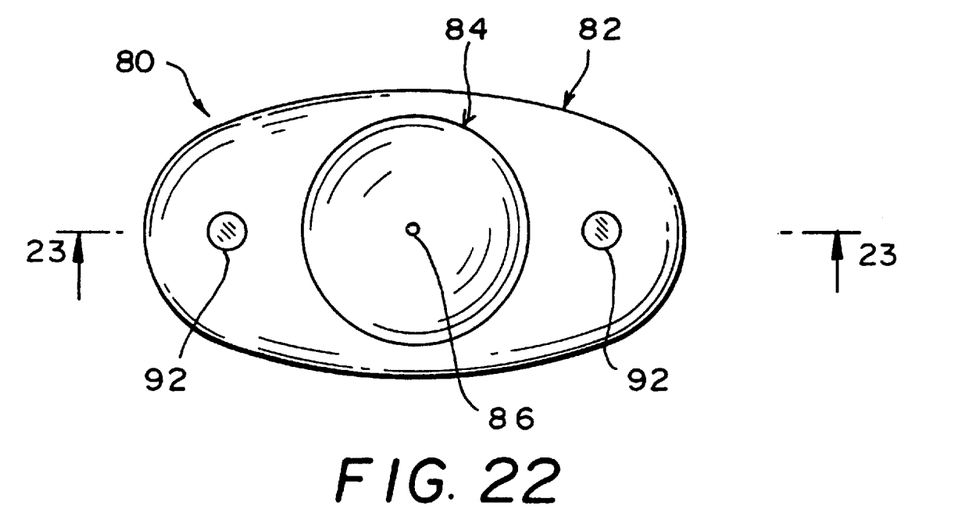
FIG. 22 is a cross-sectional view of an eye having an intraocular refractive correction lens according to the present invention implanted therein.
Figure 23:
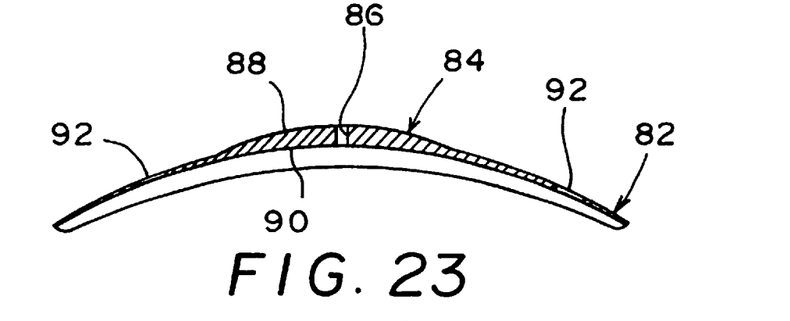
FIG. 23 is a cross-sectional view the eye with a prior art intraocular refractive correction lens implanted therein.

An embodiment of an intraocular refractive correction lens 80 having a lens body portion 82 and lens portion 84, is shown in FIGS. 22 and 23. In this embodiment, an air passageway 86 (e.g. hole) is provided in the center optical axis of the lens portion 84 for equalizing the pressure between the anterior surface 88 and posterior surface 90 of the intraocular refractive correction lens 80. This air passageway 86 allows for equalization of pressure between the anterior chamber and posterior chamber of the eye. Otherwise, a significant suction or negative pressure can occur on the anterior surface of the intraocular refractive correction lens sucking the back of the iris into contact therewith and causing damage or wear to the iris.

Figure 24:
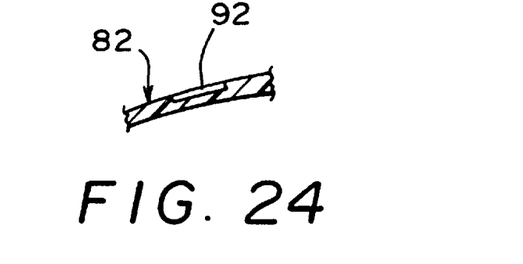
FIG. 24 is a cross-sectional view of another embodiment of an intraocular refractive correction lens.

The intraocular refractive correction lens 80 is provided with a pair of indents 92, as shown in FIGS. 22 to 24, for allowing the intraocular refractive correction lens 80 to be manipulated under the iris during the implantation operation. The indents 92 are significantly better than through holes for purposes of manipulation, since the bottoms of the indents prevent penetration of a manipulating tool through the lens and inadvertently into contact with the natural lens that would cause an immediate cataract of the natural lens.

FIG. 25 illustrates a lens implantation according to the prior art. FIG. 25 shows a natural eye 100 with posterior chamber 102 and natural crystalline lens 104 with anterior surface 106. An intraocular lens 108 is shown implanted into the posterior chamber 102 into a position at the pupil 98 wherein the posterior surface 110 of lens 108 is in intimate contact with the anterior surface 106 of natural crystalline lens 104.

In one embodiment, a dimension of the eye is determined and the intraocular lens is provided according to the eye dimension so that the intraocular lens forms a spacing when inserted into the posterior chamber. For example, the arc of radius of curvature of the natural crystalline lens can be determined by methodology known in the art. The arc of radius of curvature of the intraocular lens is then determined according to the arc of radius of curvature of the natural crystalline lens. If an intraocular lens is provided that has an arc of radius of curvature less than the arc of curvature of the natural crystalline lens, the implanted intraocular lens will form a spacing with the anterior surface of the natural crystalline lens. In another embodiment, the arc from a location on the ciliary body of the natural crystalline lens over an arc of radius of curvature of the natural crystalline lens to another location on the ciliary body of the natural crystalline lens is determined. If the intraocular lens is provided with a posterior surface having an arc greater than the determined arc, the implanted intraocular lens will form a spacing with the anterior surface of the natural crystalline lens.

Figure 26:
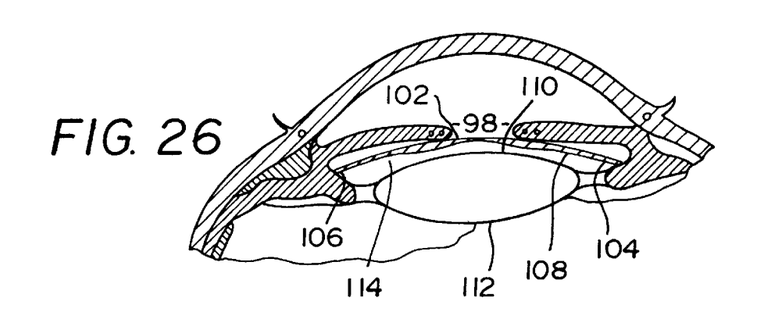
FIGS. 26–28 are partial side sectional views of a human eye with artificial intraocular lenses illustrating lens implants according to the present invention.
Figure 27:
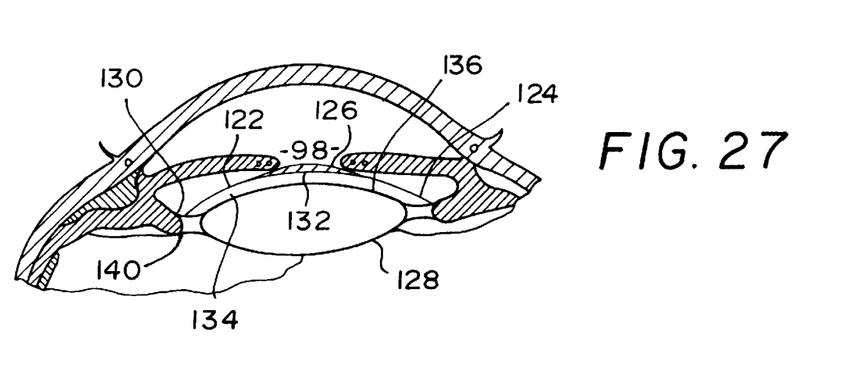
Figure 28:
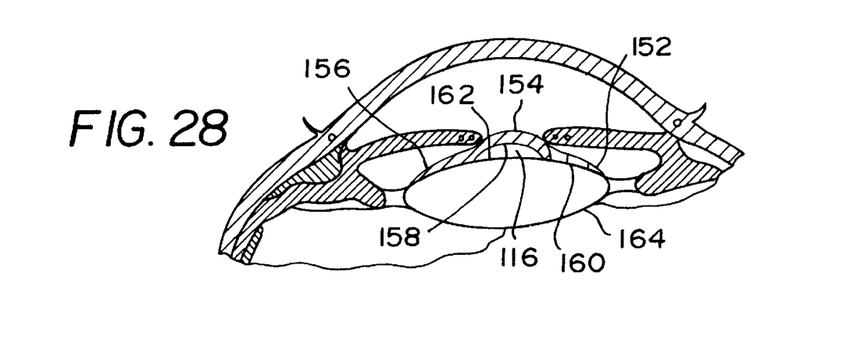

An intraocular lens according to any of FIGS. 1–24 can be implanted in a natural eye by the method of the present invention. The artificial intraocular lens is inserted into a posterior chamber of the eye to a position anterior to and in a vicinity of the natural crystalline lens to provide a spacing between the artificial intraocular lens and the natural crystalline lens as shown in FIGS. 26–28. Preferably the spacing is a separation between the posterior surface of the intraocular lens and the anterior surface of the natural crystalline lens of between 50 $\mu$m and 150 $\mu$m.

FIG. 26 illustrates one embodiment wherein the intraocular lens 102 rests at its periphery edge 104 at zonule attachment 106. In this embodiment, the radius of curvature of the arc of the posterior surface 108 of the intraocular lens 102 is less than the radius of curvature of the arc of the anterior surface 110 of the crystalline lens 112 and the arch of the arc of the intraocular lens 102 forms a vaulted relationship over the crystalline lens surface 110 at the location of the pupil 98 to form the spacing 114 of the invention. The spacing 114 is located between intraocular lens 102 and the pupil 98. As shown in FIG. 26, the intraocular lens 102 does not contact either the natural crystalline lens 112 or the iris, at any point on the lens 112 or the iris.

In another embodiment shown in FIG. 27, the intraocular lens 122 includes a body portion 124 that positions the optic portion 126 of the lens in its vaulted relationship anterior to the natural crystalline lens 128 at the location of pupil 98. A vaulted lens describes a lens having a concave posterior surface 132 that is arched to form a spacing 134 between the posterior surface 132 of the intraocular lens 122 and the anterior surface 136 of natural crystalline lens 128 when the intraocular lens 122 is implanted and seated in an eye. The vaulted arch is formed as a result of an elongated body portion 124 that is seated to extend from zonule attachment 138 at lens periphery 140 so as to form the arched structure separated by a spacing 134 from the natural lens anterior surface 136.

In still another embodiment shown in FIG. 28, the intraocular lens 152 comprises an optic portion 154 and a body portion 156. The radius of the arc of posterior surface 158 of the optic portion is smaller than the radius of the arc of the posterior surface 160 of the body portion 156 so that the respective arcs meet at an angle. The smaller radius of the arc of the optic portion 154 forms the vaulted relationship with the anterior surface 162 of the crystalline lens 164 in the location of the pupil 98 to form spacing 166. In this embodiment, the radius of the arc of the lens body 156 can be the same as the radius of the arc of the anterior surface 162 of the crystalline lens 164 so that the posterior surface 160 of the lens body portion 156 resides on the surface of the anterior surface 162 of the crystalline lens 164 in a face to face relationship. The alternate relationship is shown in FIG. 27 where the radius of the arc of the body portion 124 can be less than the radius of the arc of the anterior lens surface 136 so that the spacing 134 of the invention is formed by a combination of the vaulted optic portion and a cavity between the body portion and the crystalline lens 128.

The intraocular lens of the invention can be deformable in accordance with the lenses of the Mazzocco patents so that the lens can be implanted through a small incision made in the ocular tissue. These intraocular lenses have prescribed memory characteristics. The lenses can be deformed by compressing, rolling, folding, stretching or the like or by a combination thereof, to a diameter of 80% or less of the cross-sectional diameter of the optic. The prescribed memory characteristics permit the lenses to restore to their original configuration, full size and fixed focal length after insertion into the eye.

Preferably, the intraocular lens body of the present invention can be a silicone material or more preferably a collagenous acrylic reaction copolymer that is biologically compatible with tissue of the natural eye. These materials are known in the art as represented by U.S. Pat. No. 5,104,957 to Kelman et al. The collagenous acrylic reaction copolymers are particularly advantageous. The acrylic collagen polymer lens is permeable to both gases and nutrients. The lens has significant water content and permits free perfusion of nutrients that are required by the eye. Further while applicants do not intend to be bound by the following explanation, it is believed that an acrylic collagen polymer intraocular lens permits a permeation of ocular fluid through the lens body and into the spacing formed between the implanted intraocular lens body posterior surface and the natural crystalline lens anterior surface. A reaction may take place within the spacing. At any rate, it is known that an interphase zone is formed in the spacing. The interphase zone enhances wearing comfort of the implanted intraocular lens. Additionally the interphase provides a transition between the natural crystalline lens and implanted intraocular lens that permits adjustment of light transmission properties of the intraocular lens to light transmission properties of the natural crystalline lens so as to provide accurate vision correction.

Other modifications of the present invention will occur to those skilled in the art subsequent to a review of the present application. For example, the arch that forms the spacing can be a result of an elongated haptic lens portion that is seated so as to extend from a zonule attachment at the lens periphery so as to form an ached structure separated from the natural crystalline lens anterior surface. In this application, a haptic portion is a portion of an intraocular lens that extends from the zonule attachment at the lens periphery. The haptic portion may coincide with the base portion or the haptic may be considered only a part of a larger base portion that extends with the transition portion and optic portion to form the vault over the natural crystalline lens.

These modifications and equivalents thereof are intended to be included within the scope of this invention.

What is claimed:

1. An intraocular refractive correction lens for implanting in a posterior chamber of an eye in a vicinity of a natural crystalline lens and pupil of the eye, comprising:

a shape predetermined with respect to a shape of the natural crystalline lens to form a spacing between a posterior surface of said intraocular refractive correction lens and an anterior surface of the natural crystalline lens at a location between the natural crystalline lens and the pupil of the eye, said intraocular refractive correction lens being configured so as to not contact with the natural crystalline lens at any point when implanted in the eye.

2. The intraocular refractive correction lens of claim 1, wherein said intraocular refractive lens is configured to provide an interphase zone formed in said spacing.

3. The intraocular refractive correction lens of claim 2, wherein said interphase zone is 50 µm to 150 µm thick.

4. The intraocular refractive correction lens of claim 1, comprising an optic portion and base portion.

5. The intraocular refractive correction lens of claim 4, comprising an optic portion having an essentially planar anterior surface.

6. The intraocular refractive correction lens of claim 4, comprising a vaulted optic portion with convex anterior surface and concave posterior surface that forms said spacing.

7. The intraocular refractive correction lens of claim 4, comprising a transition portion that defines an elliptically transcribed surface transition from a surface of said optic portion to a surface of said base portion.

8. The intraocular refractive correction lens of claim 1, comprising a posterior surface in a concave shape in an arc having a radius of curvature less than a radius of curvature of an arc of the anterior surface of the natural crystalline lens that forms said spacing.

9. The intraocular refractive correction lens of claim 1, comprising an acrylic collagen polymer.

10. The intraocular refractive correction lens of claim 1, comprising a silicone material.

11. The intraocular refractive correction lens of claim 1, wherein said intraocular refractive corrective lens does not contact with an iris of the eye at any point.

12. An intraocular refractive correction lens for implanting in the vicinity of a natural crystalline lens and pupil of an eye, comprising:

a shape predetermined with respect to a shape of the natural crystalline lens to form a spacing between a posterior surface of said intraocular refractive correction lens and an anterior surface of the natural crystalline lens at a location between the natural crystalline lens and pupil when said intraocular refractive correction lens is implanted in the eye, said intraocular refractive correction lens not contacting the natural crystalline lens at any point when implanted in the eye.

13. The intraocular refractive correction lens of claim 12, comprising an optic portion and base portion.

14. The intraocular refractive correction lens of claim 13, comprising an optic portion having an essentially planar anterior surface.

15. The intraocular refractive correction lens of claim 14, comprising a transition portion that defines an elliptically transcribed surface transition from a surface of said optic portion to a surface of said base portion.

16. The intraocular refractive correction lens of claim 13, comprising a vaulted optic portion with convex anterior surface and concave posterior surface that forms said spacing.

17. The intraocular refractive correction lens of claim 12, comprising a posterior surface in a concave shape in an arc having a radius of curvature less than a radius of curvature of an arc of the anterior surface of the natural crystalline lens of an eye.

18. The intraocular refractive correction lens of claim 12, comprising an acrylic collagen polymer.

19. The intraocular refractive correction lens of claim 12, comprising a silicone material.

20. The intraocular refractive correction lens of claim 12, compressed into a diameter of less than a length of an incision in the eye for insertion through the incision into the eye.

21. The intraocular refractive correction lens of claim 12, wherein said intraocular refractive corrective lens is configured so as to not contact with an iris of the eye at any point.

22. An intraocular refractive correction lens for implanting in a posterior chamber of an eye in a vicinity of a natural crystalline lens and pupil of the eye, comprising:

a shape predetermined with respect to a shape of the natural crystalline lens to form a spacing between a posterior surface of said intraocular refractive correction lens and an anterior surface of the natural crystalline lens at a location between said intraocular refractive correction lens and the pupil, said intraocular refractive correction lens being configured so as to not contact an iris of the eye at any point when implanted in the eye.

23. The intraocular refractive correction lens of claim 22, wherein said intraocular refractive lens is configured to provide an interphase zone formed in said spacing.

24. The intraocular refractive correction lens of claim 23, wherein said interphase zone is 50 µm to 150 µm thick.

25. The intraocular refractive correction lens of claim 22, comprising an optic portion and base portion.

26. The intraocular refractive correction lens of claim 25, comprising an optic portion having an essentially planar anterior surface.

27. The intraocular refractive correction lens of claim 25, comprising a vaulted optic portion with convex anterior surface and concave posterior surface that forms said spacing.

28. The intraocular refractive correction lens of claim 25, comprising a transition portion that defines an elliptically transcribed surface transition from a surface of said optic portion to a surface of said base portion.

29. The intraocular refractive correction lens of claim 22, comprising a posterior surface in a concave shape in a arc having an radius of curvature less than a radius of curvature of an arc of the anterior surface of the natural crystalline lens that forms said spacing.

30. The intraocular refractive correction lens of claim 22, comprising an acrylic collagen polymer.

31. The intraocular refractive correction lens of claim 22, comprising a silicone material.

32. An intraocular refractive correction lens for implanting in the vicinity of a natural crystalline lens and pupil of an eye, comprising:

a shape predetermined with respect to a shape of the natural crystalline lens to form a spacing between a posterior surface of said intraocular refractive correction lens and an anterior surface of the natural crystalline lens at a location between the natural crystalline lens and pupil when said intraocular refractive correction lens is implanted in the eye, said intraocular refractive correction lens not contacting an iris of the eye at any point when implanted in the eye.

33. The intraocular refractive correction lens of claim 32, comprising an optic portion and base portion.

34. The intraocular refractive correction lens of claim 33, comprising an optic portion having an essentially planar anterior surface.

35. The intraocular refractive correction lens of claim 34, comprising a transition portion that defines an elliptically transcribed surface transition from a surface of said optic portion to a surface of said base portion.

36. The intraocular refractive correction lens of claim 33, comprising a vaulted optic portion with convex anterior surface and concave posterior surface that forms said spacing.

37. The intraocular refractive correction lens of claim 32, comprising a posterior surface in a concave shape in an arc having a radius of curvature less than a radius of curvature of an arc of the anterior surface of the natural crystalline lens of an eye.

38. The intraocular refractive correction lens of claim 32, comprising an acrylic collagen polymer.

39. The intraocular refractive correction lens of claim 32, comprising a silicone material.

40. The intraocular refractive correction lens of claim 32, compressed into a diameter of less than a length of an incision in the eye for insertion through the incision into the eye.

41. An intraocular refractive correction lens for implanting in a posterior chamber of an eye in a vicinity of a natural crystalline lens and a pupil of the eye, comprising:

an optic portion; and a base portion;

wherein a shape of said intraocular refractive correction lens is predetermined with respect to a shape of the natural crystalline lens such that said intraocular refractive correction lens does not contact the natural crystalline lens at any point when implanted in the eye.

42. The intraocular refractive correction lens of claim 41 wherein said shape of said intraocular refractive correction lens is predetermined such that said intraocular refractive correction lens does not contact an iris of the eye at any point.

43. The intraocular refractive correction lens of claim 41 wherein said optic portion comprises a vaulted optic portion formed by a difference in radii of curvature of posterior surfaces of said optic portion and said base portion.

44. The intraocular refractive correction lens of claim 41 wherein a radius of curvature of said intraocular refractive correction lens is less than a radius of curvature of the natural crystalline lens.

45. The intraocular refractive correction lens of claim 41 wherein the optic portion is substantially circular and the base portion is substantially oval; the base portion having a major diameter of about 10.5 mm, a minor diameter of about 6 mm, a radius of about 0.1 mm and a thickness of about 0.05 mm.

* * * * *